(12) United States Patent
Maltan

(10) Patent No.: US 6,415,185 B1
(45) Date of Patent: Jul. 2, 2002

(54) OBJECTIVE PROGRAMMING AND OPERATION OF A COCHLEAR IMPLANT BASED ON MEASURED EVOKED POTENTIALS THAT PRECEDE THE STAPEDIUS REFLEX

(75) Inventor: Albert A. Maltan, Stevenson Ranch, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/376,882

(22) Filed: Aug. 18, 1999

Related U.S. Application Data

(60) Provisional application No. 60/099,151, filed on Sep. 4, 1998.

(51) Int. Cl.[7] .................................................. A61N 1/36
(52) U.S. Cl. ....................................................... 607/57
(58) Field of Search ...................... 607/55–57; 600/554, 600/559

(56) References Cited

U.S. PATENT DOCUMENTS

| | | | |
|---|---|---|---|
| 4,400,590 A | 8/1983 | Michelson | 179/107 |
| 4,532,930 A | 8/1985 | Crosby et al. | 128/419 |
| 4,592,359 A | 6/1986 | Galbraith | 128/419 |
| 4,947,844 A | 8/1990 | McDermott | 128/421 |
| 5,603,726 A | 2/1997 | Schulman et al. | 607/57 |
| 5,626,629 A | 5/1997 | Faltys et al. | 607/57 |
| 5,758,651 A | * 6/1998 | Nygard et al. | 607/55 |
| 5,999,856 A | * 12/1999 | Kennedy | 607/57 |
| 6,157,861 A | * 12/2000 | Faltys et al. | 607/57 |
| 6,195,585 B1 | * 2/2001 | Karunasiri et al. | 607/57 |
| 6,205,360 B1 | * 3/2001 | Carter et al. | 607/57 |

FOREIGN PATENT DOCUMENTS

| | | | |
|---|---|---|---|
| WO | 9748447 | 12/1997 | A61N/1/36 |

* cited by examiner

*Primary Examiner*—Carl Layno
(74) *Attorney, Agent, or Firm*—Bryant R. Gold

(57) ABSTRACT

A myogenic-based evoked response (termed the "MER" for purposes of this application), heretofore considered an undesirable artifact in response to an applied Cochlear stimulus, is deliberately sensed and measured with permanently implanted electrodes connected to a Cochlear implant device. The measured MER is then used to assist in the objective programming of the Cochlear implant. The MER may be measured between two intra-Cochlear electrodes, between one intra-Cochlear electrode and one extra-Cochlear reference electrode, or between two extra-Cochlear electrodes. Because the measured MER is believed to pre-empt the actual stapedius reflex, the electrodes need not be placed into or in close proximity to the stapedial tendon, the stapes, or the facial nerve.

7 Claims, 3 Drawing Sheets

OBJECTIVE PROGRAMMING AND OPERATION OF A COCHLEAR IMPLANT BASED ON MEASURED EVOKED POTENTIALS THAT PRECEDE THE STAPEDIUS REFLEX

The present application claims the benefit of U.S. Provisional Application Serial No. 60/099,151, filed 09/04/1998, which application is incorporated herein by reference.

BACKGROUND OF THE INVENTION

The present invention relates to Cochlear implant systems, and more particularly to a technique for programming a Cochlear implant system based, in part, on measured evoked potentials that precede the stapedius reflex.

One of the more perplexing problems facing users of Cochlear implant systems, and the clinicians and physicians who implant and adjust such systems, is properly setting the stimulation parameters used by these systems. That is, each Cochlear implant system must be adjusted to "fit" an individual patient, so that sounds are properly perceived by that patient, and so that sounds are not painfully too loud, or undetectably too soft, or otherwise not intelligible by the patient. This problem is especially difficult because heretofore so much of what is deemed a "proper" setting has been a subjective determination made by the patient. Ofttimes, however, due to the age or disabilities of the patient, the patient is ineffective at accurately communicating what he or she senses or "hears" through the implant system to the attending medical personnel. There is thus a need in the implantable Cochlear stimulation art for techniques, methods and systems for more objectively "fitting" the implant system to the individual patient.

Others have addressed this "fitting" problem in various ways. U.S. Pat. No. 5,626,629, for example, provides a clinician with various adjustment tools, including the use of a personal computer (PC) having a special software program loaded therein that help the clinician set and adjust numerous stimulation parameters.

Further techniques for objectively setting stimulation parameters involve the use of special electrodes and/or circuitry adapted to sense the stapedius reflex, as disclosed, e.g., in International Publication WO97/48447, published Dec. 12, 1997, filed in the Patent Cooperation Treaty (PCT) as International Application Number PCT/US97/10590, on Jun. 19, 1997. This PCT publication is incorporated herein by reference. Electrodes for more effectively sensing the stapedius reflex are disclosed in commonly-owned U.S. patent application Ser. No. 09/323,594, filed Jun. 6, 1999, now U.S. Pat. No. 6,208,882, also incorporated herein by reference.

While monitoring and sensing the stapedius reflex provides a valuable technique for obtaining objective feedback regarding sound loudness, which information in turn is useful in setting the stimulation parameters of an implantable Cochlear stimulation system, being able to accurately sense the stapedius reflex is not an easy task, and typically involves implantation of additional extra-Cochlear electrodes and additional sensing circuitry. There is thus a need for alternative ways, other than sensing the stapedius reflex, to obtain objective data that can aid in the setting of the stimulation parameters of a Cochlear stimulation device.

An evoked potential of probably myogenic origin is known to occur at a latency of about 5 to 12 milliseconds following acoustic stimulation. This evoked potential typically occurs between wave 5 of the elicited auditory brainstem response (EABR) and before mid-latency responses. This evoked potential is larger than EABRs, and occurs at high stimulation levels only. When taking EABR measurements, this evoked potential is generally considered an undesirable artifact, and its origin may not be fully understood at this time. It is likely that this evoked potential pre-empts the actual stapedius reflex. For purposes of this patent application, this evoked potential, occurring between wave 5 of the EABR at a latency of about 5 to 12 milliseconds following acoustic stimulation, is referred to as the "myogenic evoked response" or "MER".

In the past, the MER has been measured with standard EABR electrodes, mounted at two different surface locations on the head. The MER has been measured for diagnostic purposes, i.e., for the purpose of objectively assessing functionality of the auditory nerve in response to electrical stimulation via a temporary needle electrode placed at the promontory or the round window niche. Such diagnostic application has been described by Nikos Marangos et al., of Hannover, Germany, in the early 1990's.

SUMMARY OF THE INVENTION

The present invention addresses the above and other needs by measuring the described MER with permanently implanted electrodes that are connected to a Cochlear implant device. The measured MER is then used to assist in the objective programming and/or operation of the Cochlear implant.

Unlike the prior diagnostic measurements of the MER using surface electrodes mounted on the head, the MER is measured in accordance with the present invention between implanted electrodes, e.g., between two intra-Cochlear electrodes, between one intra-Cochlear electrode and one extra-Cochlear reference electrode, or between two extra-Cochlear electrodes.

Moreover, unlike prior techniques for obtaining objective data associated with an implant device, which have focused on measuring either the reflex response of the stapedial tendon or the neural potential on the facial nerve that feeds the stapedial tendon, the present invention does not measure the actual stapedius reflex. Hence, the present invention does not require electrodes to be placed into or in close proximity to the stapedial tendon, the stapes, or the facial nerve.

In accordance with one aspect of the invention, there is provided a method of objectively gathering stimulation data associated with programming an implantable cochlea stimulation (ICS) system. Such ICS system includes an implantable electrode array having at least intra-Cochlear electrode contacts, means for applying an electrical stimulus to a selected pair of the electrode contacts, and means for sensing an evoked potential occurring between a selected pair of the electrode contacts. The method includes the following steps: (a) selecting a pair of sensing electrodes through which the MER is to be sensed; (b) applying a stimulus of a selected energy or magnitude to the cochlea; (c) monitoring the selected sensing electrodes for the occurrence of the MER during a prescribed time period after application of the stimulus; (d) readjusting the energy or magnitude of the electrical stimulus as a function of whether the MER is sensed during the prescribed time period; (e) measuring the magnitude of the sensed MER; and (f) using the measured magnitude of the MER to generate data useful in programming the ICS system.

In accordance with another aspect of the invention, there is provided an improved system for objectively programming a Cochlear stimulation system. The Cochlear stimulation system includes an implantable Cochlear electrode array, means for selectively applying an electrical stimulus to selected electrode pairs within the electrode array, and means for sensing an evoked potential between selected electrode pairs within the electrode array. The improved system provided by the invention includes: (a) means for sensing and measuring an evoked response between a selected pair of electrode pairs during a prescribed time period following application of a stimulus; and (b) means for using the measured evoked response to assist in objective programming of the Cochlear stimulation system, and/or operation of the system. If used during operation, the measured evoked response may be used as a feedback signal to adjust the level of the stimuli to be applied by the Cochlear stimuli system, i.e., as a type of bionic automatic gain control (AGC) signal.

It is thus an object of the present invention to provide a method and system for obtaining objective data associated with setting stimulation parameters of a Cochlear implant system.

It is a feature of the invention to provide such a method and system that may be used without having to measure either the reflex response of the stapedial tendon or the neural potential on the facial nerve that feeds the stapedial tendon.

It is a further object of the invention to measure and constructively use an evoked response of myogenic origin, and a response which has heretofore been generally considered an undesirable artifact, to aid in the objective programming of a Cochlear implant system.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
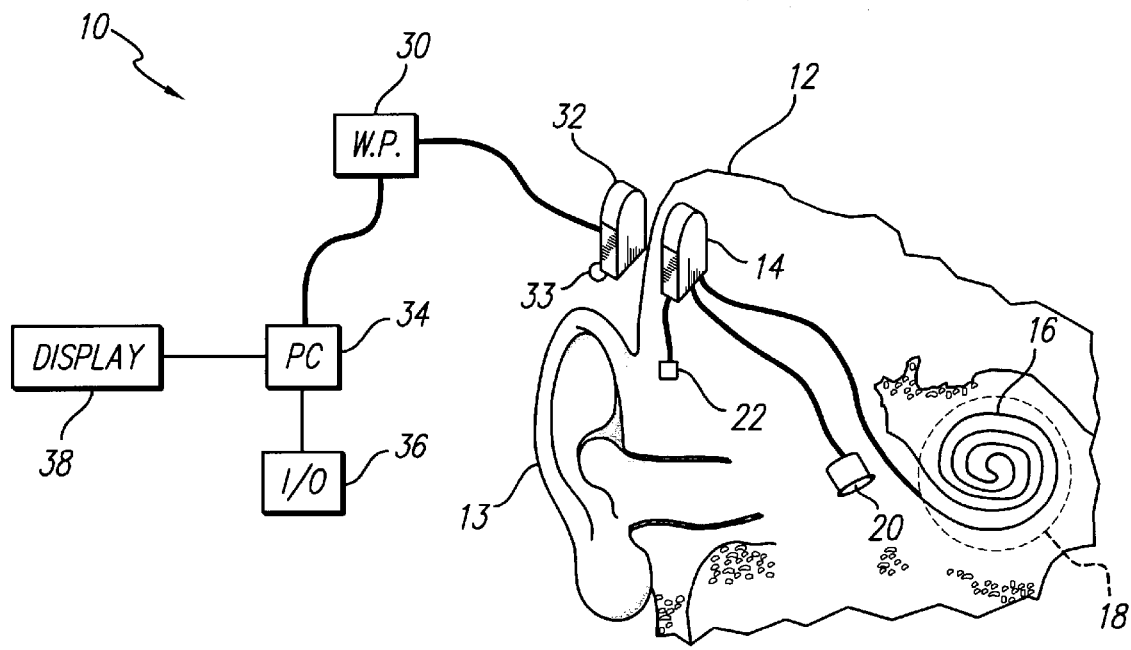
FIG. 1 schematically illustrates the main components of a representative Cochlear stimulation system.

Turning first to FIG. 1, there is shown a diagram that illustrates the main components used within a representative Cochlear stimulation system 10. As seen in FIG. 1, such system 10 typically includes implantable components and external (non-implanted) components. The implanted components include an implantable Cochlear stimulator (ICS) 14, which ICS 14 is typically implanted behind the ear 13 of a patient's head 12. An electrode array 16 is attached to the ICS 14, and is implanted within the cochlea 18 of the patient, the electrode array includes multiple spaced-apart electrode contacts, e.g., sixteen electrode contacts, that are spaced-apart within the cochlea. Because the electrode contacts are intended for positioning within the cochlea, they are commonly referred to as intra-Cochlear electrodes.

The ICS 14 may also optionally include at least one reference electrode 22 that is not implanted within the cochlea. Because such reference electrode 22 is not positioned within the cochlea, it may also be referred to as an extra-Cochlear electrode. A common location for extra-Cochlear electrodes is on the case of the ICS 14.

The ICS 14 may additionally include one or more other extra-Cochlear electrodes 20, e.g., an extra-Cochlear electrode that is placed near the middle ear, near the stapedial tendon, or near the facial nerve. While it is a feature of the invention that such extra-Cochlear electrode 20 need not be required in order to practice the invention, it is important to note that the invention may still be practiced if such an extra-Cochlear electrode is available.

The external components of the Cochlear stimulation system 10 shown in FIG. 1 include a wearable processor (WP) 30 that is attached to a headpiece 32. The headpiece 32 is held in place on the head 12 of the patient so as to be in close proximity with the implanted ICS 14. The headpiece 32 includes a microphone 33 for sensing acoustic sound. In normal operation, the sensed acoustic sounds picked up the microphone 33 within the headpiece 32 are converted to electrical signals, passed over to the WP 30, and processed in the WP in accordance with a selected speech processing strategy in order to generate a stream of stimulation control signals. The stimulation control signals are then sent to the headpiece 32 where they are transmitted (e.g., through inductive coupling) into the implanted ICS 14, and acted upon by the ICS in order to generate stimulus signals that are applied to the cochlea through the electrode contacts included within the electrode array 16. The applied stimulus signals activate cells and neurons within the cochlea, which cause nerve impulses to be sent to the patient's brain through the auditory nerve. Such nerve impulses are perceived by the patient as "sound", and thus provide the patient with the sensation of "hearing".

When "fitting" an ICS system to a patient, a personal computer (PC) 34, used as a controller, is coupled to the WP 30, as shown in FIG. 1. Such PC 34 includes one or more input/output (I/O) devices 36, such as a keyboard and/or a pointer device (e.g., a mouse), that allow the operator of the PC to set various programming parameters associated with operation of the ICS system. A display 38 is also included as part of the PC 34 in order to enable the user of the PC to see, by way of graphic displays and/or other displayed data, the settings that are made. A typical fitting process is described in U.S. Pat. No. 5,626,629, incorporated herein by reference.

A more complete description of a representative ICS system 10 may be found in U.S. Pat. No. 5,603,726, incorporated herein by reference. Other ICS systems are described, e.g., in U.S. Pat. Nos. 4,400,590; 4,532,930; 4,592,359; and 4,947,844. It is to be understood that the present invention is not directed to a particular type of ICS system, per se, and may in fact be used with almost any type of ICS system, providing the appropriate sensing and stimulation functions are included, as described below. Rather, the invention herein disclosed relates to ways of improving the manner in which an ICS system is programmed, or "fitted" to a patient, and to ways in which the ICS system operates, so that the ICS system may be more effective at carrying out its intended purpose of helping the patient accurately sense or "hear" sounds.

Figure 2:
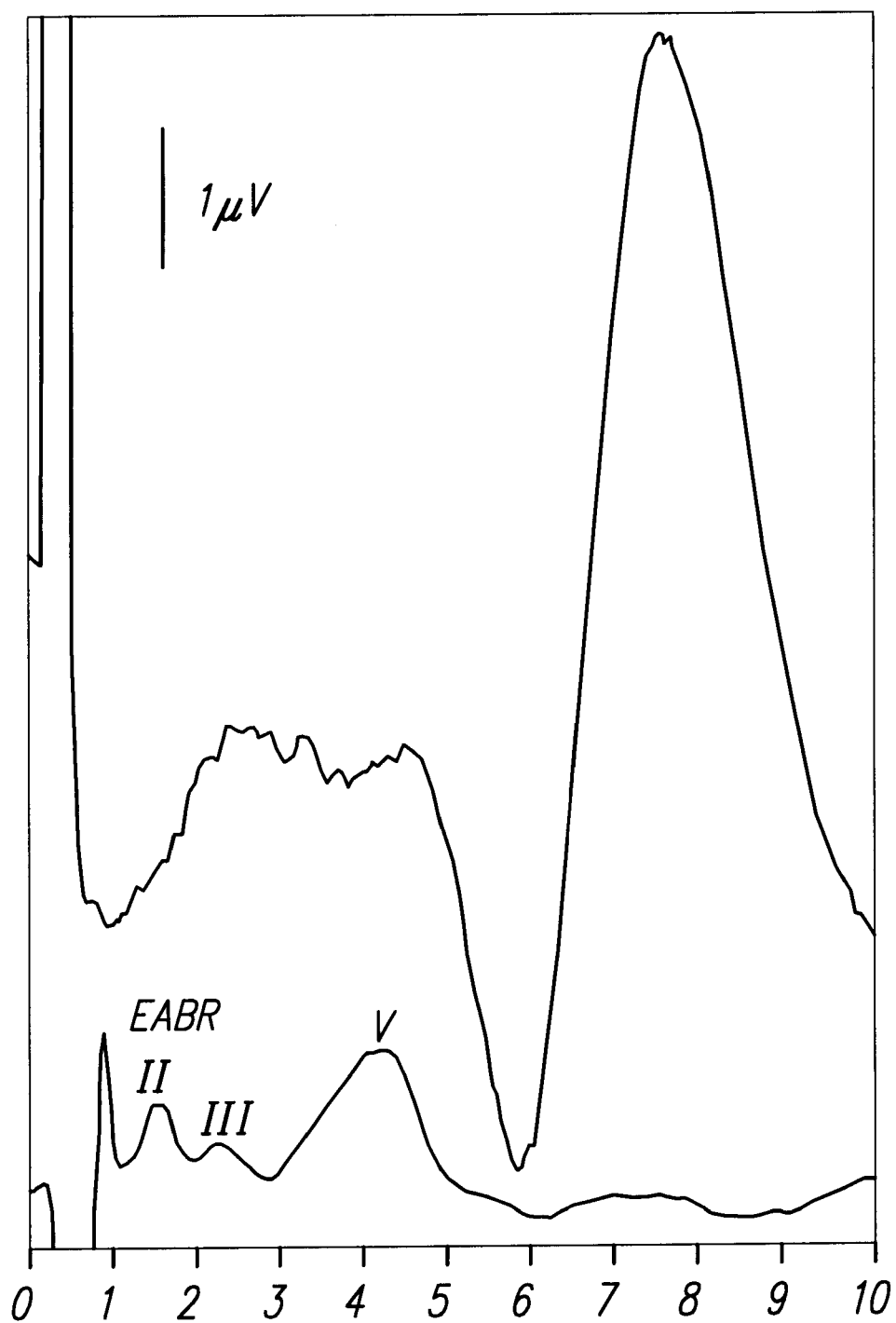
FIG. 2 is a waveform diagram that illustrates a myogenic evoked response (MER) of the type which is sensed in accordance with the invention.

Turning next to FIG. 2, there is shown a waveform diagram of a representative myogenic evoked response (MER), or an evoked muscle response (top waveform in FIG. 2), of the type sensed by the present invention. The waveform shown in FIG. 2 is from a published textbook, and as such, reflects how the MER may appear based on the sensing electrodes used. When sensed between implanted electrodes, as taught by the present invention, the actual appearance of the MER may vary from that shown in FIG. 2 depending upon the location of the electrodes, and other factors.

An ICS system that includes all of the circuitry necessary to carry out the present invention is disclosed in U.S. Pat. application serial No. 09/344,429, filed Jun. 25, 1999, now U.S. Pat. No. 6,195,585, entitled "Remote Monitoring of Implantable Cochlear Stimulator". This '585 patent is assigned to the same assignee as is the present application an d is incorporated herein by reference.

The ICS system disclosed in the '585 patent includes an input multiplexer that allows any of 16 intra-Cochlear electrodes, two stapedius electrodes, or two reference electrodes to be selected for monitoring an evoked response. The '585 patent teaches that once a pair of electrodes has been selected as the sensing electrodes, monitoring of the sensed electrodes should occur for a period of time just before application of a stimulus pulse (to a selected pair of stimulates electrodes) until about 5 milliseconds after application of the stimulus. In contrast, in accordance with the present invention, the MER of interest occurs between about 5 and 12 milliseconds after application of the stimulus. Thus, in order to practice the present invention, circuitry of the type disclosed in the '585 patent may be used, but controlled so that monitoring of the selected sense electrodes occurs during a prescribed time window that begins about 5 milliseconds after application of the stimulus and ends about 12 milliseconds after application of the stimulus.

Figure 3:
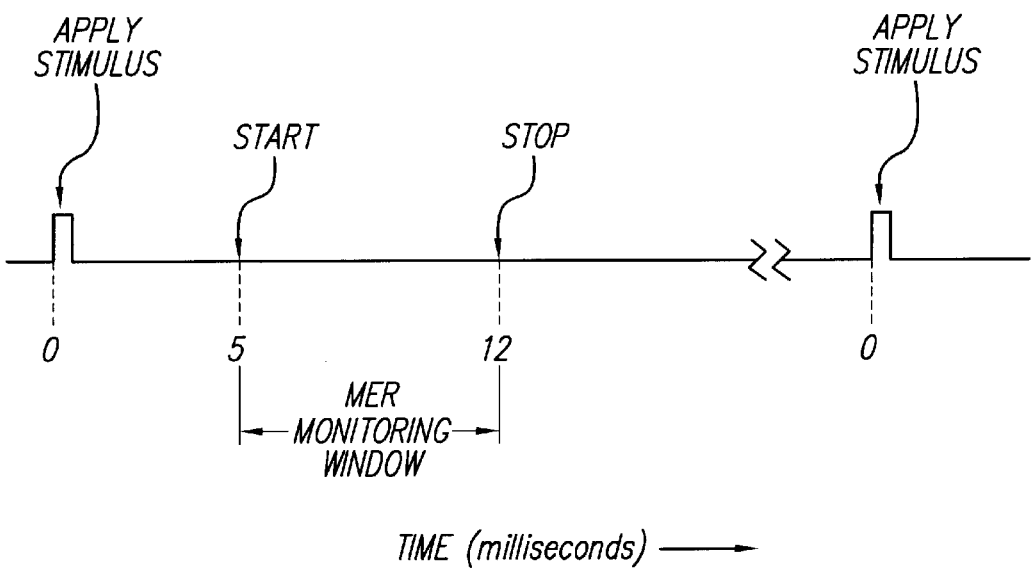
FIG. 3 is a timing diagram that illustrates an "MER Monitoring Window" for use with the invention.

A prescribed time window of the type used with the invention, referred to as the "MER Monitoring Window", is illustrated in FIG. 3. In order to determine if an MER occurs, a stimulus is applied to the patient at time t=0. Generally, such stimulus will comprise an electrical stimulus that is applied to a selected pair of implanted electrodes. However, it is also contemplated that, for patients whose middle-ear function remains intact, such applied stimulus may comprise an acoustic stimulus. Such acoustic stimulus may be applied, e.g., through a set of earphones, to the outer ear of the patient.

With reference to FIG. 3, it is seen that monitoring for the occurrence of the MER starts at a time about 5 milliseconds after application of the stimulus. Such monitoring continues until about 12 milliseconds after application of the stimulus, at which time the monitoring stops, i.e., the MER Monitoring Window closes. Monitoring may continue through application of another stimulus, some time later, as also shown in FIG. 3. It is thus evident that for the timing shown in FIG. 3 the MER Monitoring Window remains open for about 5 milliseconds. It is to be understood that the start and stop times illustrated in FIG. 3 are intended to be exemplary only, and not limiting. The start time and duration of the MER Monitoring Window may be changed, as required, in order to better sense the MER or similar artifacts that prove useful in providing objective data associated with application of a stimulus (electrical or acoustic) to the patient, programming of the ICS system, and operation of the ICS system.

Figure 4:
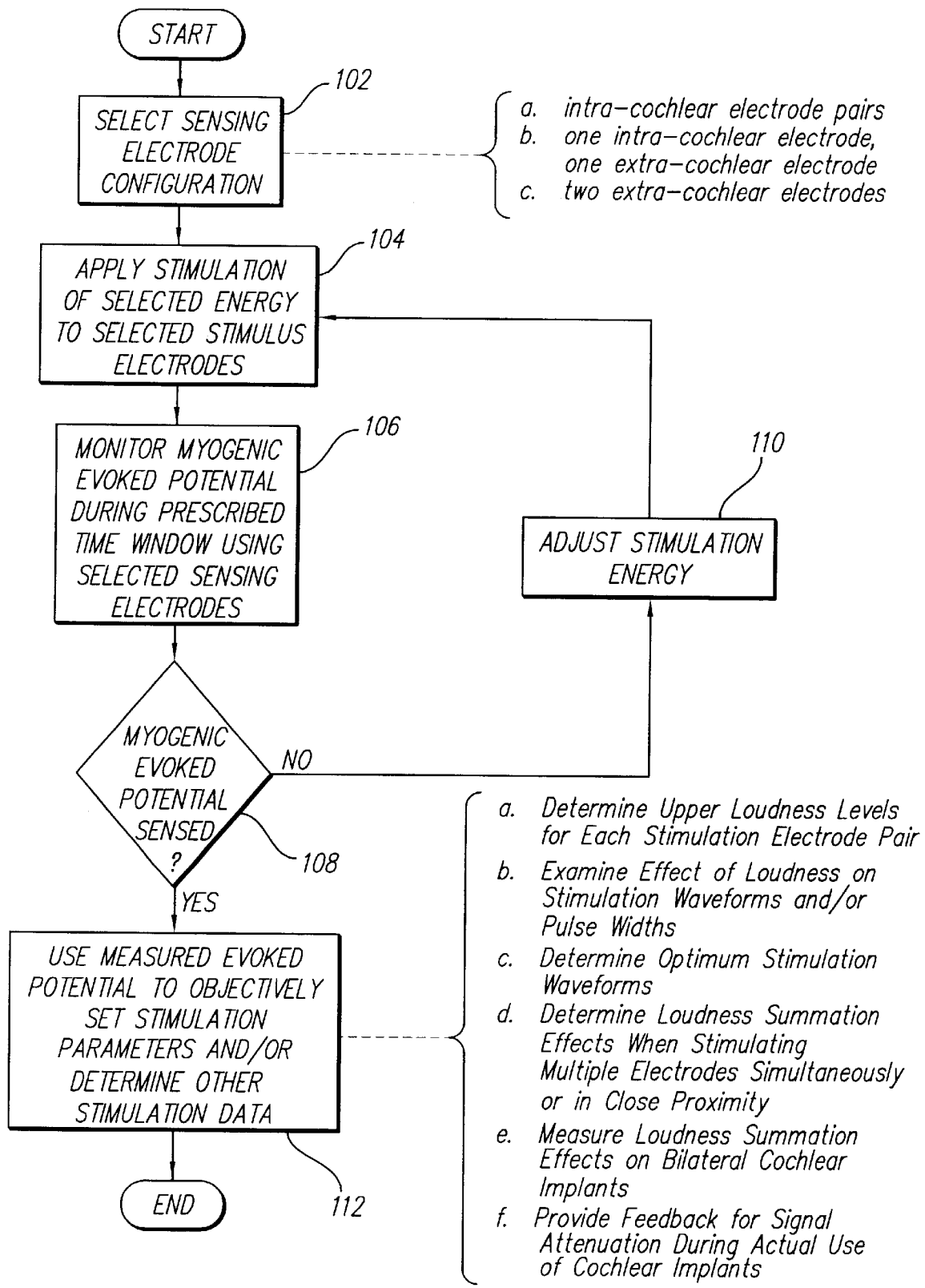
FIG. 4 is a flow chart that illustrates the main steps associated with a method of measuring the MER in accordance with the invention.

Turning next to FIG. 4, a flow chart is presented that depicts the main steps utilized in carrying out the method of the invention. Such method includes, as an initial step, selecting a desired sensing electrode configuration (block 102). Such sensing electrode configuration may include intra-Cochlear electrode pairs, one intra-Cochlear electrode paired with one extra-Cochlear electrode, or two extra-Cochlear electrodes. After a sensing electrode configuration is selected and enabled, a stimulus is applied to the patient (block 104). While block 104 of FIG. 4 suggests that such stimulus is an electrical stimulus which is applied to a selected pair of stimulus electrodes, it is to be understood, as indicated above, that the stimulus may also comprise an acoustic stimulus applied to the patient, e.g., through an earphone, if the patient has a functioning middle ear.

After application of the stimulus, the MER Monitoring Window is opened at the prescribed time following application of the stimulus, and remains open for a prescribed time thereafter (block 106), as shown in the timing diagram of FIG. 3.

While the MER Monitoring Window remains open, the selected sensing electrodes are monitored for the occurrence of the MER. (Note, the MER is also referred to in FIG. 4 as the "Myogenic Evoked Potential"). If no MER is sensed (NO branch of block 108), then a new stimulus may be applied with an adjusted energy (block 110), and the process repeated (blocks 104, 106, 108).

If an MER is sensed (YES branch of block 108), the such MER is measured, and the measured MER is then available to help objectively set stimulation parameters and/or determine other stimulation data (block 112). For example, as shown in FIG. 4, the measured MER may be used to: (a) determine upper loudness levels for each stimulation electrode pair; (b) examine the effect of loudness on stimulation waveforms and/or pulse widths; (c) determine optimum stimulation waveforms; (d) determine loudness summation effects when stimulating multiple electrodes simultaneously or in close proximity; (e) measure loudness summation effects on bilateral Cochlear implants; or (f) provide feedback for signal attenuation during actual use of the Cochlear implant. The latter use of the measured MER—to provide feedback for signal attenuation during actual use of the Cochlear implant—is particularly attractive because it allows a type of bionic automatic gain control (AGC) to be used by the ICS system which prevents the patient from ever sensing or "hearing" sounds that are too loud (e.g., painfully loud, which is a recurring problem with many existing ICS systems). Advantageously, such automatic gain control inherently takes into consideration, as part of the control loop, the signal variations and limitations of the external-to-implant link (e.g., the inductive coupling link).

While the invention herein disclosed has been described by means of specific embodiments and applications thereof, numerous modifications and variations could be made thereto by those skilled in the art without departing from the scope of the invention set forth in the claims.

What is claimed is:

1. A method of objectively gathering stimulation data associated with programming an implantable cochlea stimulation (ICS) system, the ICS system including an implantable electrode array having intra-cochlear electrode contacts, at least one extra-cochlear electrode contact, means for applying an electrical stimulus to a selected pair of the electrode contacts, and means for sensing an evoked potential occurring between a selected pair of the electrode contacts, the method comprising:

selecting a pair of sensing electrodes that includes the at least one extra-cochlear electrode contact through which an evoked potential is to be sensed;

applying a stimulus of a selected magnitude;

monitoring the selected sensing electrodes for the occurrence of an evoked potential during a prescribed time period, wherein the prescribed time period comprises a time window that begins about 5 milliseconds, and ends about 12 milliseconds, following application of the stimulus;

readjusting the energy of the electrical stimulus as a function of whether the evoked potential is sensed during the prescribed time period;

measuring the magnitude of the evoked potential sensed during the prescribed time period; and using the measured magnitude of the evoked potential to generate data useful in programming the ICS system.

2. The method of claim 1 wherein the step of using the measured magnitude of the evoked potential to generate data useful in programming the ICS system comprises using the data for at least one of the following purposes: determining upper loudness levels for each stimulus electrode, examining the effect of loudness of stimulation waveforms and/or stimulation pulse widths, determining optimum stimulation waveforms, determining loudness summation effects when stimulating multiple electrodes simultaneously or in close proximity, measuring loudness summation effects on bilateral Cochlear implants, or providing feedback for signal attenuation during use of the ICS system.

3. In a cochlear stimulation system, including an implantable cochlear electrode array, means for selectively applying an electrical stimulus to selected electrode pairs within the electrode array, and means for sensing an evoked potential between selected electrode pairs within the electrode array, an improved system for objectively programming the cochlear stimulation system, comprising:

means for sensing and measuring an evoked response between a selected pair of electrode pairs during a prescribed time period following application of a stimulus that commences about 5 milliseconds after application of the stimulus and lasts for approximately 5 milliseconds thereafter; and means for using the measured evoked response to assist in objective programming of the cochlear stimulation system.

4. In a cochlear stimulation system, including an implantable cochlear electrode array, means for selectively applying an electrical stimulus to selected electrode pairs within the electrode array, and means for sensing an evoked potential between selected electrode pairs within the electrode array, an improved system for objectively operating the cochlear stimulation system, comprising:

a sensor that detects and measures an evoked response between a selected pair of electrode pairs during a prescribed time period following application of a stimulus, wherein the prescribed time period comprises a time period that commences about 5 milliseconds after application of the stimulus and lasts for approximately 5 milliseconds thereafter; and processing circuitry that uses the measured evoked response as a feedback signal to set the level of the electrical stimulus applied to a selected electrode pair within the electrode array.

5. A method of objectively gathering stimulation data associated with programming an implantable cochlea stimulation (ICS) system, the ICS system including an implantable electrode array having intra-cochlear electrode contacts, means for applying an electrical stimulus to a selected pair of the electrode contacts, and means for sensing an evoked potential occurring between a selected pair of the electrode contacts, the method comprising:

selecting a pair of sensing electrodes through which an evoked potential is to be sensed;

applying a stimulus of a selected magnitude;

monitoring the selected sensing electrodes for the occurrence of an evoked potential a prescribed time period after application of the stimulus, wherein the prescribed time period comprises a time window that begins about 5 milliseconds, and ends about 12 milliseconds, following application of the stimulus;

readjusting the energy of the electrical stimulus as a function of whether the evoked potential is sensed during the prescribed time period;

measuring the magnitude of the evoked potential sensed during the prescribed time period; and using the measured magnitude of the evoked potential to generate data useful in programming the ICS system.

6. The method of claim 5 wherein the ICS system further includes at least one extra-cochlear electrode contact, and wherein the step of selecting a pair of sensing electrodes includes selecting a pair of sensing electrodes that includes said at least one extra-cochlear electrode contact.

7. The method of claim 5 wherein the step of using the measured magnitude of the evoked potential to generate data useful in programming the ICS system comprises using the data for at least one of the following purposes: determining upper loudness levels for each stimulus electrode, examining the effect of loudness of stimulation waveforms and/or stimulation pulse widths, determining optimum stimulation waveforms, determining loudness summation effects when stimulating multiple electrodes simultaneously or in close proximity, measuring loudness summation effects on bilateral cochlear implants, or providing feedback for signal attenuation during use of the ICS system.

* * * * *